(12) United States Patent
Eshelman et al.

(10) Patent No.: US 6,611,206 B2
(45) Date of Patent: Aug. 26, 2003

(54) AUTOMATIC SYSTEM FOR MONITORING INDEPENDENT PERSON REQUIRING OCCASIONAL ASSISTANCE

(75) Inventors: Larry J. Eshelman, Ossining, NY (US); Srinivas Gutta, Buchanan, NY (US); Daniel Pelletier, Lake Peekskill, NY (US); Hugo J. Strubbe, Yorktown Heights, NY (US); John Milanski, Boulder, CO (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 20 days.

(21) Appl. No.: 09/809,613

(22) Filed: Mar. 15, 2001

(65) Prior Publication Data

US 2002/0171551 A1 Nov. 21, 2002

(51) Int. Cl.⁷ ............................................. G08B 23/00
(52) U.S. Cl. ..................... 340/573.1; 340/531; 340/522; 340/541; 600/300; 600/301; 705/2; 128/920; 348/143
(58) Field of Search ............................ 340/573.1, 573.4, 340/573.7, 552, 555, 540, 531, 539, 521, 522, 641; 396/153, 312; 382/181; 705/2, 3; 128/920–925; 348/14.01, 148, 14.03, 152–155, 143; 600/300, 301; 702/188

(56) References Cited

U.S. PATENT DOCUMENTS

| | | | |
|---|---|---|---|
| 4,524,243 A | 6/1985 | Shapiro | 179/5 |
| 5,544,649 A | 8/1996 | David et al. | 600/301 |
| 5,617,855 A * | 4/1997 | Waletzky et al. | 600/586 |
| 5,802,494 A * | 9/1998 | Kuno | 705/2 |
| 5,905,436 A | 5/1999 | Dwight et al. | 340/573.1 |
| 6,002,994 A | 12/1999 | Lane et al. | 702/188 |
| 6,049,281 A * | 4/2000 | Osterweil | 340/573.4 |
| 6,174,283 B1 * | 1/2001 | Nevo et al. | 600/301 |
| 6,198,394 B1 * | 3/2001 | Jacobsen et al. | 340/573.1 |
| 6,270,456 B1 * | 8/2001 | Iliff | 600/300 |
| 6,416,480 B1 * | 7/2002 | Nenov | 600/557 |
| 6,475,143 B2 * | 11/2002 | Iliff | 600/300 |
| 6,524,239 B1 * | 2/2003 | Reed et al. | 600/300 |

FOREIGN PATENT DOCUMENTS

| | | | |
|---|---|---|---|
| DE | 3830655 | 9/1988 | G08B/23/00 |
| EP | 0716402 | 12/1995 | G08B/13/193 |
| GB | 2027312 | 7/1979 | G01S/3/78 |
| GB | 2179186 | 7/1986 | G08B/21/00 |
| WO | WO9725697 | 1/1997 | |

* cited by examiner

Primary Examiner—Benjamin C. Lee
(74) Attorney, Agent, or Firm—Gregory L. Thorne

(57) ABSTRACT

Briefly, an alarm system monitors conditions of an independent person, yet one requiring some supervision, such as an elderly person living alone at home. The system monitors a variety of independent signals and combines them to recognize subtle cues that may indicate there will be a need for intervention by a supervisor.

19 Claims, 3 Drawing Sheets

AUTOMATIC SYSTEM FOR MONITORING INDEPENDENT PERSON REQUIRING OCCASIONAL ASSISTANCE

BACKGROUND OF THE INVENTION

1. Field of the Invention

The present invention relates to automatic devices that generate an alarm signal when conditions surrounding an unsupervised person indicate the person requires assistance.

2. Background

Remote security monitoring systems in which a video camera is trained on a subject or area of concern and observed by a trained observer are known in the art. Also infant or child monitors that transmit audio to a portable receiver are available in the market. These devices, however, require constant attention in order to provide protection to the subject or area of concern, such as an elderly person, infant, or child.

Machine identification of faces is a technology that is well developed. In GB 2343945A for a system for photographing or recognizing a Face, a controller identifies moving faces in a scene and tracks them to permit image capture sufficient to identify the face or distinctive features thereof. For example, in a jewelry store security system, the system could sound an alarm upon recognizing a pulled-down cap or facemask.

A monitored person's physical and emotional state may be determined by a computer for medical diagnostic purposes. For example, U.S. Pat. No. 5,617,855, hereby incorporated by reference as if fully set forth herein, describes a system that classifies characteristics of the face and voice along with electroencephalogram and other diagnostic data to help make diagnoses. The device is aimed at the fields of psychiatry and neurology. This and other such devices, however, are not designed for monitoring persons in their normal environments.

EP 0716402B1 describes a method of detecting the number of people entering a train or other space using infrared sensors and fuzzy inference techniques. When the number of people is outside desired limits or unbalanced, the system can generate notices to that effect which may be linked to devices to correct the condition.

UK 2027312A describes a method of detecting the movement of fish using IR cameras generating a standard video signal.

U.S. Pat. No. 4,524,243 describes a system in which a user is required to activate a switch at specified intervals. Failure to do so results in the generation of an inactivity alarm.

U.S. Pat. No. 5,905,436 discloses a system in which the failure of various sensors in a home to be triggered results in the generation of a signal at a central monitoring station indicating such. The disclosure is directed at the supervision of an elderly person living at home.

UK 2179186A describes a system in which, if movement is not detected at a pre-determined time, an alarm is triggered. A warning is given so that the user can reset the switch.

U.S. Pat. No. 6,002,994 discloses a system in which transmitters, placed at strategic locations in a house, are triggered whenever a person is present at the location of a sensor triggering the transmitter. Also, the system employs other inputs attached to devices and appliances that the user is expected to use. The system is trained to recognize normal patterns of use. The transmitters transmit a signal to a central monitor if the normal pattern is not detected.

In this reference, physiological measurements may include the user's blood pressure, heart rate, body temperature, body weight, and blood glucose level. Non-physiological measurements may include room temperature, ammonia from spilled urine, methane from spoiling food, a presence of smoke, frequency of electrical usage, frequency of water usage, temperature of water flowing from a tap, the user's movement within the selected environment as indicated by motion sensors, and use of appliances including a toilet, telephone, stove, microwave oven, toaster, oven, refrigerator, freezer, dishwasher, bath, shower, garbage disposal means, clothes washer, clothes drier, mail box, door and vehicle.

In another application area, machines automatically detect an occupant's presence or specific features of the occupant for purposes of machine-authorization and authentication or convenience. To that end, some prior art systems employ biometric sensing, proximity detectors, radio frequency identification tags, or other devices.

Although automated systems for monitoring the activities of elderly persons have been proposed, there exists a need for enhanced robustness of such systems and an ability to avoid the signaling of false positives and, more importantly, earlier intervention. For example, an elderly person falling out of the sensor range for an extended period could be disabled from a life-threatening problem yet escape detection by a system such as proposed in U.S. Pat. No. 6,002, 994. Subtle queues that humans can detect, and that may indicate a problem before it occurs, are not detectable by prior art systems. Also, alarm information may not be sufficiently informative. As a result of these and other drawbacks, machine-monitoring of persons that are alone is not nearly up to the standard afforded by a living attendant.

SUMMARY OF THE INVENTION

Briefly, an alarm system monitors conditions of an independent person, yet one requiring some supervision, such as an elderly person living alone at home. The system monitors a variety of independent signals and combines them to recognize subtle cues that may indicate there will be a need for intervention by a supervisor.

As computers are used more widely, and processing power makes possible the use of inexpensive sensors, the ability to control without direct human intervention has become widely discussed. For example, in the home of the future, the heating system, lighting, music systems, appliances, etc. may all migrate toward a regime in which they control themselves rather than requiring the user to control them. In these models, the user's intentions are inferred by his/her actions. Presence may trigger heat or light activation; television activation may trigger dimming of lights and closing of curtains. In such environments, inexpensive sensor technology is leveraged by computing power to produce useful responses in the system. Future homes may be filled with sensors permitting many features to be implemented by software modifications alone. In such an environment, a rich array of sensor data can be harnessed for many purposes heretofore unrecognized. The present application combines this data in ways that allow useful patterns to be detected in the manner that a human observer can detect subtle patterns. The object application, in this case, is the monitoring of an independent person such as a sick or elderly person.

The invention contemplates an environment employing pervasive sensors, including video and audio, with the application of artificial intelligence technology to permit the recognition of such subtle cues as mood swings, irregular behavior, and presence of unrecognized persons, objects, or animals. When conditions are classified as requiring or suggesting a need for intervention, an informative alarm signal or message containing information about the situation is transmitted to help the recipient understand what is going on. In an embodiment, the alarm signal is a live video and/or audio feed from a camera trained on the person requiring care. In another embodiment, the alarm signal is a symbolic set of data relating to the status and the condition that generated the alarm, for example, the message "Person requiring care idle for N hrs," "Presence of unrecognized face," "Physiognomy indicates distress," or "Abnormally high level of activity." In still other embodiments, the system generates responses to stimulate action, such as a response from the monitored person to elicit a recognized behavior or other machine-sensible profile. The alarm signal may be transmitted by phone line, the Internet, or a wireless channel. In still other embodiments, the sensors can adjust themselves, for example, a camera that can zoom on the facial features of an occupant to capture a recognizable image or video sequence.

The field of artificial intelligence and robotics has given rise to technology that enables machines to make sufficient sense of their surroundings to recognize predefined conditions, navigate vehicles, and identify objects and their orientations, for example. Components of systems called autonomous observers have been made in the lab which allow a machine to follow an observer in an area and track escape routes. Other applications of similar technology include video tracking systems that follow a speaker giving a presentation and respond to the speaker's gesture commands. In embodiments of the present invention, the technology of image and video recognition, audio recognition, and other inputs may be used to infer the condition of a monitored person requiring care.

Artificial Intelligence (AI) principles are used by a classification engine receiving video, audio, and/or other inputs to model a current situation. When conditions are classified as calling for attention (distress event), video, audio, and other data that may be buffered up to the distress event, as well as live data, may be transmitted to a monitor along with an indication of the class to which the recognized event belongs. For example, the audio signal generated by a crying person requiring care may be classified as a "person crying" condition either alone or in concert with the classification of other data such as video data of the crying person requiring care. Condition classes for a monitor system may include events such as:

1. trigger by a physiological sensor such as a halter heart monitor, breathing sensor, or audio sensor,
2. detection of an unrecognized voice, face, body, or object,
3. abnormal movement of the person such as indicative of an injury, for example, limping,
4. sudden movement consistent with falling, running, normal walking, crawling, etc.,
5. lack of normal movement such as palsy, lack of coordination, too fast as in addressing an emergency, or movement that is abnormally slow,
6. presence of the person requiring care or other individuals in a space and their number,
7. consistency of the clothing, facial features, etc. of the occupants of a space throughout a period of time.
8. loud sounds, normal sounds, and unusual sounds, based upon signature of sound,
9. unusual location of sound sources,
10. occupancy of unauthorized spaces,
11. occupancy patterns, for example whether monitored person is spending unusual amounts of time in a particular space or away from a particular space,
12. patterns suggesting damage to the monitoring system, or objects in the occupied space,
13. voice signatures of unauthorized occupants or unrecognized voice signatures,
14. body habitus and physiognomy of monitored person or other occupants,
15. status of security system in the space,
16. unrecognized objects in occupied spaces or recognized objects being moved or found in unexpected locations,
17. temperature, humidity, sound levels, or other ambient variables out of normal range,
18. presence of an unrecognized face or body pattern, An event that triggers an alarm condition may be a simple one such as prior art sensors that monitor breathing or crying, or it may be more complex one that integrate multiple inputs into a software (or hardware) network (e.g., neural; Bayesian) that is programmed or configured to identify or recognize the circumstances, or absence of identifiable (familiar) circumstances. Based on this data, the system ultimately classifies the circumstance as an alarm condition or not. Such network devices may include classifiers in the form of neural networks, Bayesian networks, and other techniques for machine-recognition of physical objects and behaviors. The art in this field is rich and rapidly-growing and it is expected that improved means for implementing the current invention will continually become available.

Preferably the classification engine is trainable so that it does not need to rely solely on predefined template patterns for pattern-matching. In an embodiment, however, the raw data is distilled by AI classifiers, such as a video classifier, into a distilled signal permitting explicit rules to be defined in a further stage of classification as to whether an alarm condition exists or not.

The system may be provided with the ability to generate a simulated dialogue to provide for assistance in training, such as asking an occupant to select from among a number of condition classes present in a monitored space at a time when the occupant can observe the monitored space. This may be used by the system to reduce the ambiguity of its combined signals. For example, the simulated dialogue may be generated using "chatterbot" technology with a machine-generated persona such as disclosed in the following references, each of which is incorporated in its entirety as if fully set forth herein.

U.S. patent Ser. No. 09/699,606 for Environment-Responsive User interface/Entertainment Device That Simulates Personal Interaction;

U.S. patent Ser. No. 09/686,831 for Virtual Creature Displayed on a Television; and U.S. patent Ser. No. 09/699,577 for User interface/ Entertainment Device That Simulates Personal Interaction and Responds to Occupant's Mental State and/or Personality.

The persona may, in response to a particular condition (ambiguous classification of extant conditions or just on a random or interval time basis) request information from occupants about present circumstances. The feedback received may be used by the classification engine to further infer the extant conditions and/or relayed to a responsible party along with other information about circumstances. The above applications also discuss the topic of classifying large arrays of inputs to make decisions about occupants.

The invention will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE PREFERRED EMBODIMENTS

Figure 1:
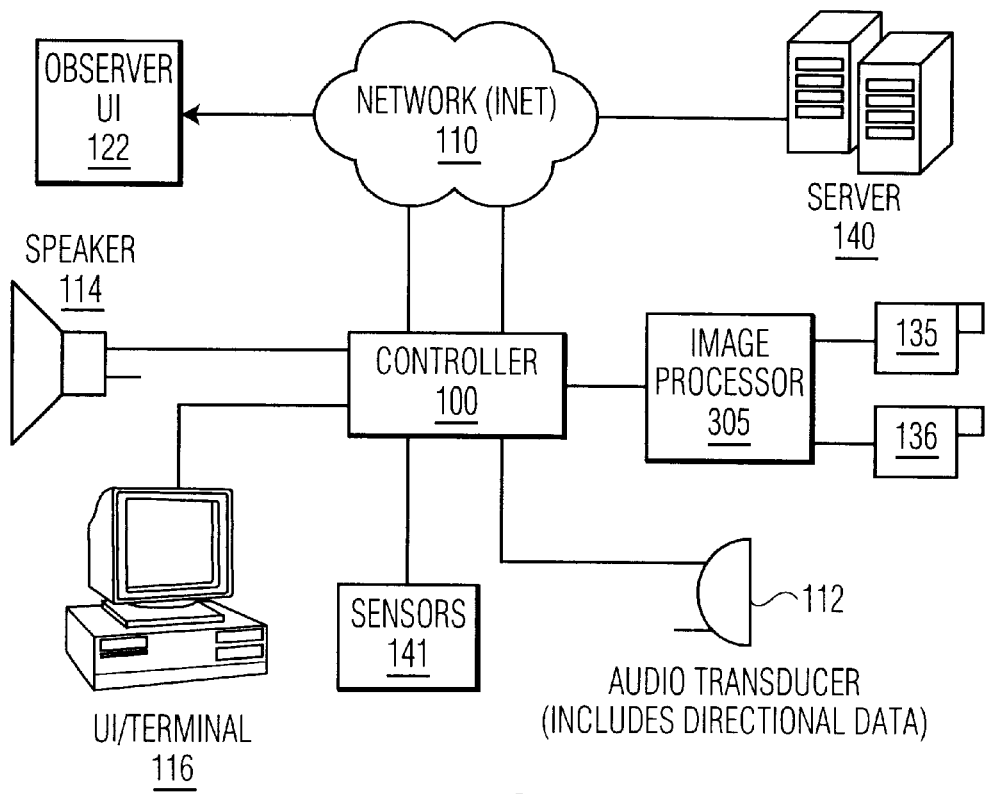
FIG. 1 is a schematic representation of a hardware system capable of supporting a monitor system according to an embodiment of the invention.

Referring to FIG. 1, in a hardware apparatus for implementing an embodiment of the invention, a programmable controller 100 receives input from various sources, for example, a connected image processor 305 connected to cameras 135 and 136, microphone 112, and sensors 141. Sensors 141 may include alarm sensors such as breathing monitors or any type of sensor such as temperature sensors, position sensors, security switches, proximity sensors, electrical load sensors, ambient light sensors, etc. Data for updating the controller's 100 software or providing other required data, such as templates for modeling its environment, may be gathered through local or wide area or Internet networks symbolized by the cloud at 110. A remote observer may keep track of, or receive alarm signals from the system via a UI 122 (e.g., terminal). The controller may output audio signals (e.g., synthetic speech or speech from a remote speaker) through a speaker 114 or a device of any other modality. For programming and requesting occupant input, a terminal 116 may be provided.

Figure 2:
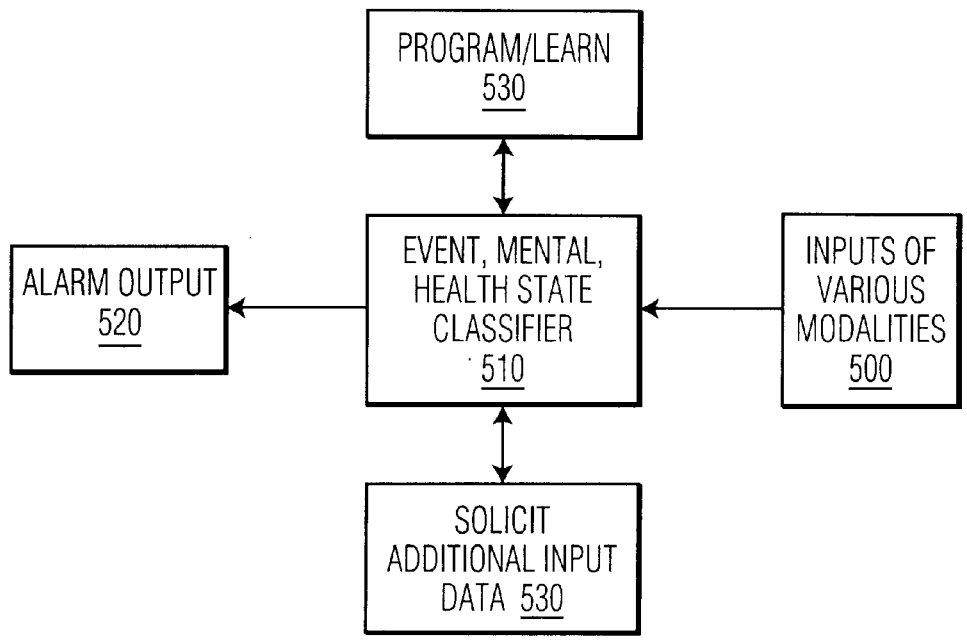
FIG. 2 is a high level flow diagram illustrating how inputs of various modalities may be filtered to generate an alarm signal consistent with several embodiments of the invention.

FIG. 2 illustrates how information gathered by the controller 100 of FIG. 1 may be used to identify particular conditions and generate an alarm responsive to those conditions. Inputs of various modalities 500 such as video data, audio data, environmental conditions such as temperature, sound level, security system status, etc. are applied to a trained classifier 510 to discriminate and classify distinguishable features of a monitored environment. For example, the classifier 510 may be trained to discriminate faces and to classify them as belonging to one of a recognized set or not belonging to any member of the recognized set. For another example, the classifier 510 may be trained to classify sudden noises like breaking glass or falling objects. Still other examples include recognition of the emotional status and health of the monitored person by facial expression, physiognomy, body habitus, behavior, etc. from data in a video signal. Each classification of events/status may then be combined and further classified as an alarm condition. For example, the classifier may be trained to identify a loud sound followed by an unrecognized face as an alarm condition.

The technologies for training such classifiers as 510 are well developed and growing fast. Such classifiers may be trained explicitly using rules to form, for example, a Bayesian classifier. Alternatively, they may be trained using examples, as for a neural net. Since the subject of how different kinds of classifiers are designed and trained is not the focus of the present invention, except as discussed herein, and because the technology for designing and training such classifiers is well-developed and highly varied, the particulars are not discussed in detail presently. Some interface for programming and/or training the classifier 510 is indicated 530. The end goal of the classifier 510 is to output status or alarm information to an alarm output 520. Both 530 and 520 may be networked terminals, cell phone devices, PDAs, or any suitable UI device.

Figure 3:
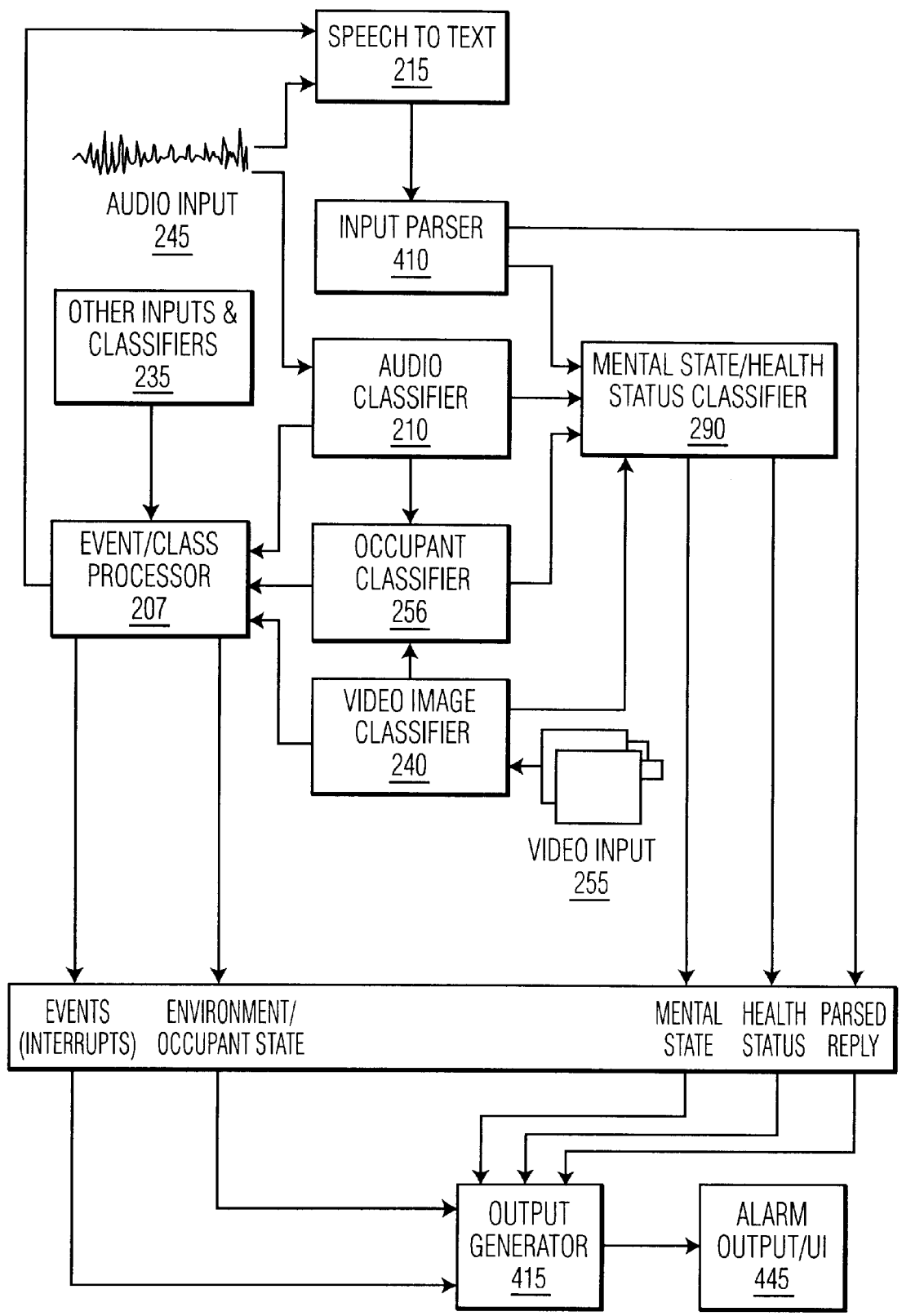
FIG. 3 is a functional diagram of a software system for implementing a monitor system according to an embodiment of the invention.

Referring now to FIG. 3, a functional diagram of an event driven architecture that may be used to monitor an occupied zone separates the object illustrated by the single "black box" of classifier 510, into multiple objects whose outputs are combined to classify alarm conditions. Audio input 245, video input 255, and other user interface devices (not shown) generate signals that are applied to respective classifiers 210, 240. The audio input 245, which may be received by a microphone (not shown separately) or a directional audio detector (not shown separately) which indicates both the sound and its direction, or any other suitable audio transducer, may be applied to an audio classifier 210. The latter data form a real-time signal, which the audio classifier 210 classifies by suitable digital or analog means or a combination thereof. The audio classifier 210 then generates a current state information signal which it applies to both a mental state/health status classifier 290 and an event/class processor 207.

The audio signal classifier may output a vector that includes the following components.
1. Identity of speaker,
2. Number of speakers,
3. Type of sound (crashing, bumping, periodic, tapping, etc.),
4. Sound intensity level,
5. Duration, time of day, of distinguished sound,
6. Quality of speech (whispering, yelling, rapid, tense, hyper, etc.),
7. Quality of voice (masculine, feminine, child, weak, strong, rough, clear, etc.),
8. An event identifiable from the sound such as the sound of switching of a light, snoring, tinny sound of a radio or TV, vacuum cleaner, etc.

Each instance of a discrete sound event and/or state may be combined with a time stamp indicating the time it began and, if it has, ended, and the combined vector signal applied to the event/class processor 207.

A video image classifier 240 receives video input 255, classifies image data, and generates state information signals which are applied to the mental state/health status classifier 290 and the event/class processor 207. The video image classifier 240 may be programmed to identify certain events such as gestures, rapid movement, number of occupants in its field of view, etc. Like the audio classifier 210, its output may be a vector, which, for illustrative purposes, includes the following components.

1. Number of occupants,
2. Identity of occupants (including unrecognized) which may derive information from body, facial features, movement, etc.,
3. Body position/gesture of each occupant (e.g., standing, seated, drinking, eating,
4. Sizes of transient objects in scene,
5. Nature of transient objects in scene (e.g., television, dinner plate, laundry basket, etc.),
6. Rapidity of movement of image center of occupants as an indication of running or chaos,
7. Change in camera angle, etc.

Video processing techniques from various fields such as authentication, gesture control of machines, etc. may be employed in the current system according to the particular aims of the system designer.

Other input devices, with associated classifiers 235, apply their output signals to the event/class processor 207. The other UI classifiers 235 may include instrumentation monitoring the environment such as ambient light level, time of day, temperature of the room, security status of a building, etc.

Text data may be obtained from a speech to text converter 215, which receives the audio input 245 and converts it to text. When obtained from audio, the text may be time-stamped by the speech to text converter 215. The speech to text converter 215 parses the text using grammatical or structural rules such as used in new or prior art conversation simulators, as used in natural language search engines, or other suitable means. The result of this parsing is the extraction of words or utterance features that the mental state/health status classifier 290 may recognize. Parsing may be done using rule-based template matching as in conversation simulators or using more sophisticated natural language methods. Words indicative of mood may then be sent to the mental state/health status classifier 290 for classification of the mood of the speaker.

The mental state/health status classifier 290 receives signals from the various classifiers and processes these to generate a mood/personality state signal. The mental state/health status classifier 290 may be a trained neural network, a Bayesian network, a simple rule-based system, or any other type of classifier capable of taking many different inputs and predicting a probability of the occupant being in a given emotional state and having a given personality. Various personality and mood typologies may be used, running from simple to complex. An example of set of rules for classifying an occupant as bored is:

low sentence/phrase word count (the occupant's sentences contain few words) (input parser 410 signal indicating response word count), a low incidence of words suggesting enthusiasm such as superlatives (input parser 410 signal indicating adjectives), a quiet flat tone in the voice (audio classifier 210 signal indicating modulation inflection intensity), a lack of physical movement (video image classifier 240 signal indicating, etc., little movement of the head or body, sighing sounds, etc.

looking at watch.

lack of eye contact with objects such as television or book in the scene.

Each of these may be classified by the corresponding classifier. The color of the occupant's clothes, the pitch of the occupant's voice, the number of times the occupant enters and leaves a single scene, the way the occupant gestures, etc. all may provide clues to the occupant's emotional state and/or personality. The output vector may be any suitable mental state classification. For example, the valence/intensity emotional state typology suggested in U.S. Pat. No. 5,987,415 may be used.

The following tables summarize the Big Five which is an evolutionary outgrowth of the Myers-Briggs typology. There are many academic papers on the subject of modeling emotional states and personalities and many of these address the issues of machine classification based on voice, facial expression, body posture, and many other machine-inputs. Even the weather, which may be obtained using an agent over the Internet or via instruments measuring basic weather data such as daily sunshine, may be used to infer mental emotional state.

The Six Facets of Negative Emotionality (adapted from Costa & McCrae, 1992) with Anchors for the Two Extremes of the Continuum

| Six Facets of Negative Emotionality | RESILIENT R+ – | REACTIVE R– |
|---|---|---|
| Worry | Relaxed; calm | Worrying; uneasy |
| Anger | Composed; slow to anger | Quick to feel anger |
| Discouragement | Slowly discouraged | Easily discouraged |
| Self-Consciousness | Hard to embarrass | More easily embarrassed |
| Impulsiveness | Resists urges easily | Easily tempted |
| Vulnerability | Handles stress easily | Difficulty coping |

The Six Facets of Extraversion (adapted from Costa & McCrae, 1992) with Anchors for the Two Extremes of the Continuum

| Six Facets of Extraversion | INTROVERT E– | EXTRAVERT E+ |
|---|---|---|
| Warmth | Reserved; formal | Affectionate; friendly, intimate |
| Gregariousness | Seldom seeks company | Gregarious, prefers company |
| Assertiveness | Stays in background | Assertive; speaks up; leads |
| Activity | Leisurely pace | Vigorous pace |
| Excitement-seeking | Low need for thrills | Craves excitement |
| Positive Emotions | Less exuberant | Cheerful; optimistic |

The Six Facets of Openness (adapted from Costa & McCrae, 1992) with Anchors for the Two Extremes of the Continuum

| Six Facets of Openness | PRESERVER O– – | EXPLORER O+ |
|---|---|---|
| Fantasy | Focuses on here and now | Imaginative; daydreams |

-continued

| Six Facets of Openness | PRESERVER O– – | EXPLORER O+ |
| --- | --- | --- |
| Aesthetics | Uninterested in art | Appreciates art and beauty |
| Feelings | Ignores and discounts feelings | Values all emotions |
| Actions | Prefers the familiar | Prefers variety; tries new things |
| Ideas | Narrower intellectual focus | Broad intellectual curiosity |
| Values | Dogmatic; conservative | Open to reexamining values |

The Six Facets of Agreeableness (adapted from Costa & McCrae, 1992) with Anchors for the Two Extremes of the Continuum

| Six Facets of Agreeableness | CHALLENGER A– | ADAPTER A+ |
| --- | --- | --- |
| Trust | Cynical; skeptical | See others as honest & well-intentioned |
| Straightforward-ness | Guarded; stretches truth | Straightforward, frank |
| Altruism | Reluctant to get involved | Willing to help others |
| Compliance | Aggressive; competitive | Yields under conflict; defers |
| Modesty | Feels superior to others | Self-effacing; humble |
| Tender-Mindedness | Hardheaded; rational | Tender-minded; easily moved |

The Six Facets of Conscientiousness (adapted from Costa & McCrae, 1992) with Anchors for the Two Extremes of the Continuum

| Six Facets of Conscientiousness | FLEXIBLE C– | FOCUSED C+ |
| --- | --- | --- |
| Competence | Often feels unprepared | Feels capable and effective |
| Order | Unorganized; unmethodical | Well-organized; neat; tidy |
| Dutifulness | Casual about obligations | Governed by conscience; reliable |
| Achievement Striving | Low need for achievement | Driven to achieve success |
| Self-Discipline | Procrastinates; distracted | Focused on completing tasks |
| Deliberation | Spontaneous; hasty | Thinks carefully before acting |

The emotional state/health status classifier 290 outputs a state vector, with a number of degrees of freedom, that corresponds to the models of personality and mental state chosen by the designer. The mental state/health status classifier 290 may cumulate instantaneous data over a period of time in modeling personality, since this is a persistent state. The mental state will have more volatile elements.

The health status may be classified by training the classifier to recognize certain features such as facial expression and pathology visible in the visage; body habitus, body movement and posture, for example slowness of movement or other abnormalities such as limping, palsy, etc. Health and mental state classification may be responsive to similar events such as the failure of an elderly person to wear pajamas or change clothes, which might signal loneliness or depression as well as some physical problem such as medication problems. The audio input from a telephone may be observed for word choice that signals problems.

Privacy may be protected by merely indicating a composite parameter rather than a content of speech. Certainly alarm signals may be tailored to protect privacy. For example, the content of the alarm signal may be less detailed where the condition may not be emergent or the status of the monitored person is not completely clear.

The mental state/health status classifier 290 may output a health status classifier that contains a list of pathologies it is trained to recognize. This may or may not coincide with purely clinical or medically recognized or distinct pathologies. Also, the system may be trained to filter out certain pathology classes or levels of severity so that it is sensitive to changes. For example, it may be insensitive to a conspicuous degree of palsy, but responsive to an increase or decrease in The event/class processor 207 is a classifier that combines state information from multiple classifiers to generate an environment/occupant state signal indicating the current status of the system's environment, including the occupants, particularly the monitored person. The event/class processor 207 may also generate event signals (interrupt signals) to ensure an instant response when certain events are recognized by the classifiers, for example, events that may coincide with an emergency condition. The recognition of events may require state information from multiple classifiers, so the event/class processor 207 combines state data from multiple classifiers to generate a combined state signal and a combined event signal. The environment/state signal may include an indication of all the possible event classes the various classifiers are capable of identifying or only those surpassing a threshold level of confidence.

The output generator 415 receives the mood/personality state vector and health status vector from the mental state/health status classifier 290 and the parsed reply data from the input parser 410. The response generator 415 also receives the environment/occupant state signal and events signal from the event/class processor 207. The output generator 415 selects a type of response corresponding to the mental state, the environment/occupant state, and the events signal from an internal database and generates an alarm output if required. Alternatively, the output generator may be programmed to select an output template that solicits further data from the monitored person or other occupant through a user interface, such as the terminal 116 (FIG. 1). For example, if the various classifier output components indicate low confidence levels, the system could generate speech through the speaker 114 asking for information about the current state of the occupied space. For example "Is anyone there" could be generated if no clear presence of an adult can be detected. The system then uses its other input devices, such as video input 255, to decrease ambiguity in its status and event signals. Note that these features may be implemented through a conversation simulator as described in U.S. patent Ser. Nos. 09/699,606, 09/686,831, and 09/699,577 may be built into the system to operate as a machine assistant.

Tracing the data flow beginning with the video input 255, the video input 255 signal is applied to the video image classifier 240. The video image classifier 240 is programmed to recognize a variety of different image and video-sequence classes in the video input 255 signal. For example, it may be programmed to distinguish between a person sitting up and lying down; between a person sitting still and one moving agitatedly or leaving a particular place; etc. A probability for each of these classes may be generated and output as a signal. Alternatively, a single, most-probable class may be generated and output as a signal. This signal is applied to the event/class processor 207, which combines this data with other class data to generate an environment/occupant state signal. If the event/class processor 207 receives an indication from the video image classifier 240 that something sudden and important has occurred, for example, the monitored person or other occupant has gotten up and left the room, the event/class processor 207 will generate an event signal. If the mental state/health status classifier 290 receives a signal from the video image classifier 240, indicating the occupant is moving in a fashion consistent with being agitated, that mental state/health status classifier 290 may combine this information with other classifier signals to generate a mood/personality state vector indicating an emotional state of heightened anxiety. For example, the audio classifier 210 may be contemporaneously indicating that the speaker's voice is more highly pitched than usual and the input parser 410 may indicate that the word count of the most recent utterances is low.

Note that to allow the system to determine whether a current class or state represents a change from a previous time, the event/class processor 207 and the mental state/ health status classifier 290 may be provided with a data storage capability and means for determining the current occupant so that corresponding histories can be stored for different occupants. Identification of occupants, as mentioned above, may be by face-recognition by means of the video image classifier 240, or by means of voice signature. It may also be confirmed by radio frequency identification (RFID) token, smart card, or a simple user interface that permits the occupant to identify him/herself with a biometric indicator such as a thumbprint or simply a PIN code. In this way, both the mental state/health status classifier 290 and event/class processor 207 may each correlate historical data with particular occupants and employ it in identifying and signaling trends to the output generator 415.

The event/class processor 207 receives class information from the audio classifier 210 and other classifiers and attempts to identify these with a metaclass it is trained to recognize. That is, it combines classes of states to define an overarching state that is consistent with that multiple of states. The architecture described herein is not the only way to implement the various features of the invention and the event/class processor 207 could simply be omitted and its functions taken over by the output generator 415. One advantage of separating the functions, however, is that the event/class processor 207 may employ a different type of classifier than the one used by the output generator 415. For example, the output generator 415 could use a rule-based template matcher while the event/class processor 207 could use a trained neural network-type classifier. These allocations of functions may be more suitable since the number of outputs of the output generator 415 may be much higher than the number of classes the event/class processor 207 (or the other classifiers) is trained to recognize. This follows from the fact that network-type classifiers (such as neural network and Bayesian network classifiers) are difficult to train when they have a large number of possible output states.

The video image classifier 240 process may contain the ability to control the cameras (represented by video input 255) that receive video information. The video image classifier 240 may contain a process that regularly attempts to distinguish objects in the room that may or may not be individuals and zoom on various features of those individuals. For example, every time a video image classifier identifies a new individual that image classifier may attempt to identify where the face is in the visual field and regularly zoom in on the face in order to obtain facial expression information which can be used for identifying the individual or for identifying the mood and/or health of the individual.

We note that the invention may be designed without the use of artificial intelligence (AI) technology as described above, although of robustness of AI technology makes it highly desirable to do so. For example, an audio signal may be filtered by a bandpass filter set for detection of loud crashing sounds and a detector that sets a time-latch output when the filter output is above certain level. Concurrently, a video luminance signal may be low pass filtered and when its energy goes beyond a certain level, it also sets a time-latch. If both latched signals go positive (loud sound and great activity in temporal proximity), the system may generate an alarm.

Alarm signals may include simply some kind of notification of an alarm status. Preferably, however, alarms should be informative as possible within the specified design criteria. For example, an alarm signal may contain audio and/or video data preceding and following the event(s) that triggered the alarm status. These could be recorded by the output generator 415 and transmitted by email, streamed through a cell-phone connection or wireless multimedia device with video capability, or some other means. Symbolic representations of the most significant state classes that gave rise to the meta-classification of the alarm condition may also be transmitted. For example, a symbol indicating "loud noise" and/or unrecognized occupant may be transmitted to, say, a text pager used by a responsible party.

Figure 4:
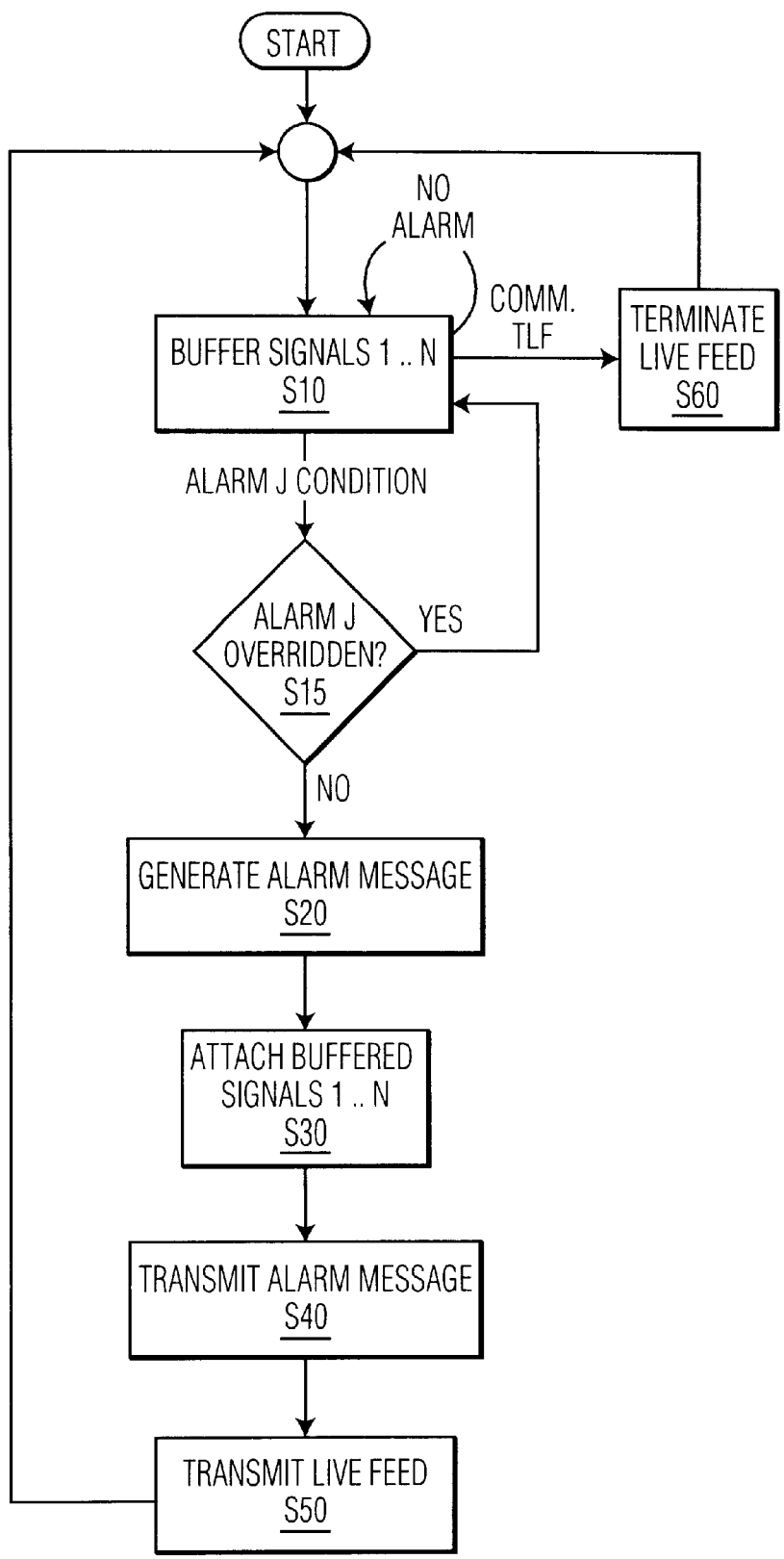
FIG. 4 is a flow chart illustrating the generation of an alarm signal according to an embodiment of the invention.

Referring now to FIG. 4, an arbitrary number of signals may be buffered continuously as illustrated by step S10. If an alarm condition is indicated, at step S15 it is determined if the particular alarm condition had been previously overridden. If it had, buffering of signals is resumed and no further action is taken. If the alarm condition had not been overridden, a message is generated at step S20 and the buffered signals 1 . . . N attached at step S30. The alarm message is then transmitted, for example by email, in step S40 and an optional live feed generated at step S50 if appropriate. The live feed may be made available at a URL included in an email transmission or as a portion of a signal in a message transmitted by an automated telephone call to a digital video telephone.

The buffered signal may be no more than a time sequence indicating the status of one or more sensors over time. The buffered signals need not be signals that caused the indication of an alarm condition. For example, in an embodiment of the invention, a video camera may be trained on a person's bed. The alarm may be generated by a mechanical sensor (such as a chest strap) that detects breathing. The video signal buffer up till the moment of the detection of the person's cessation of breathing may be the signal that is transmitted as part of the alarm message. The length of the buffer may be as desired.

Each alarm may be a unique event, but each may also be generated by the same persistent condition, for example a failure of an infant or child to breathe for a period of time. It is desirable for a given alarm to be acknowledged so that a new alarm condition, arising from different circumstances, is not confused as the existing alarm currently being attended to. One way to handle this is to assign a signature to each alarm based on a vector of the components that gave rise to the alarm condition. The recognition of the same alarm condition would give rise to another vector which may be compared to a table of existing alarms (at step S15) to see if the new alarm had already been overriden. The components may be quantized to insure against small differences in vector components being identified as different or a low sensitivity comparison may be used to achieve the same effect.

Alarm signals may be transmitted by any of the following means.

1. Automatic telephone call with synthetic voice providing symbolic indication of alarm condition (pre-recorded phrases or synthetic speech) and/or buffered audio and/or live audio fed from the monitored space.
2. Wireless appliance with video may include the above plus recorded and/or live data plus text messages providing same information.
3. E-mail message, may contain links to a URL with live or recorded data or may have embedded MIME attachment providing still or moving images.
4. Broadcast: radio message, audio message, display on a wired console, etc.

The following are several example applications and use scenarios.

EXAMPLE 1

Cameras 135, 136 are aimed at a child sleeping in a crib. A microphone 112 is placed in a position to pick up sounds near the crib. The controller 100 receives live video and audio signals from the camera and microphone and filters them through respective classifiers 240, 210 and the other classifiers 290 and 207 that combine signals. The controller 100 is programmed to recognize the normal look of the baby's face. It produces a signal indicating that a face is present and a reliability estimate indicating how well the face matches expectation. The controller 100 may be programmed to recognize other faces as well, such as relatives of the baby, children, and pets. The controller 100 is further programmed to recognize the sound of crying and produce a signal indicating that crying is present. In addition, the controller 100 is programmed to recognize the following events and produce corresponding signals: normal and abnormal body habitus of the infant, facial expression of infant indicating bad mood such as crying, content, playing, distressed, moving quickly or slowly, the number of individuals present, presence of new objects in the room and their "blob" sizes ("blob" is a term of art characterizing any closed connected shape that an image processor can define in a video image), mood of recognized face of caretaker.

In the above example, the following events may occur. The infant cries and an alarm signal is generated. The infant is restless suggestive of illness (fever). The infant's mood is detected by the audio and video signals received indicating the infant is sleeping normally.

In the event of an alarm condition, a synthetic voice calls to the caretaker via the speaker 114 requesting assistance for the infant. The alarm signal includes a text message, buffered video and buffered audio from a time prior to the alarm event. The alarm signal is sent by intercom.

EXAMPLE 2

An elderly person lives at home. The system has multiple video and audio cameras located throughout the house. Using these sensors, the system is able to recognize that the activity level of the person is low causing an increase in a generalized negative health classification signal output by the mental state/health status classifier 290. It is also able to recognize an increase in certain pathology, such as arthritis in the elderly person's hip causing the probability level corresponding to the arthritis pathology status to increase. It is also trained to recognize frustration in detecting the elderly person's utterance of periodic clipped speech using words indicative of a negative mood. This causes the mental state/health status classifier 290 to generate a high probability level in its output signal corresponding to a bad mood. It also recognizes an unusual amount of sleeping and the mental state/health status classifier 290 indicates a high probability of depression.

EXAMPLE 3

The configuration (including programming) of Example 2 is incorporated in the present example. An unrecognized face appears in view of one of the cameras. This causes the event/class processor 207 to output an indication that an unknown party has entered the home of the elderly person. The mental state/health status classifier 290 outputs a signal indicating emotional distress in response to the audio classifier indication of shouting voices. The output generator combines the mental state/health status classifier 290 and event/class processor 207 signals and generates an alarm signal.

What is claimed is:

1. A device for monitoring a first person, in a zone, who may intermittently require supervision, comprising:
   a controller programmed to receive at least one monitor signal from an environment monitor located in a monitored zone;
   said monitor signal including at least one of a image data, a video signal, and an audio signal;
   said controller being programmed to be responsive to a change in at least one of a physical pathology and a mental state detectable in said monitor signal and to generate an alarm signal responsively thereto, herein said alarm signal includes at least a portion of said monitor signal immediately prior to an incidence of said alarm condition.

2. A device as in claim 1, wherein said controller is programmed to implement a network model responsive to produce respective outputs for multiple physical pathologies.

3. A device as in claim 1, wherein said at least one monitor signal includes an image of a face of said first person.

4. A device as in claim 1, wherein said at least one monitor signal includes an audio signal representing speech, said controller being programmed to detect word patterns in said speech, said alarm signal being responsive to said word patterns.

5. A device as in claim 1, wherein said controller is programmed to distinguish between a normal voice of said person and an abnormal voice of said speaker and to generate said alarm signal responsively thereto.

6. A device as in claim 1, wherein said alarm signal includes at least a portion of said monitor signal immediately after an incidence of said alarm condition.

7. A device as in claim 1 wherein said alarm signal includes at least one of an audio signal, text data signal, and a video signal.

8. A device as in claim 1, wherein said zone is a living space of said person.

9. A device as in claim 1, wherein said alarm signal is in the form of a symbolic representation of the changed condition.

10. A method of monitoring a person requiring occasional supervision, comprising the steps of:

programming network model to classify a change in at least one of a mental state and a health status of said person responsively to at least one of a video, image, or audio signal;

using said network model to generate a first signal indicative of said at least one of a mental state and a health status to generate a class signal;

outputting a signal to elicit a behavior from said person to produce other class data;

combining said class signal with said other class data and determining an alarm condition responsively thereto;

transmitting a signal responsive to said class signal to a remote supervisor responsively to a result of said step of determining.

11. A device as in claim 10, wherein said signal responsive to said class signal is in the form of a symbolic representation of the changed condition.

12. A method of monitoring an individual in a residence, comprising the steps of:

receiving a video signal;

determining pattern of movement of said person in said residence responsively to said video signal over a period of time;

detecting a change in said pattern of movement responsively to a result of said step of determining;

generating a alarm signal responsively to a result of said step of detecting, wherein said alarm signal includes at least a portion of said video signal immediately prior to an incidence of said alarm condition.

13. A device as in claim 12, wherein said alarm signal is in the form of a symbolic representation of said changed pattern of movement.

14. A method of monitoring a person living alone, comprising the steps of:

detecting first and second signals;

filtering each of said first and second signals through a respective classifier to detect at least one of a physiological and a mental change in the monitored person;

generating a alarm responsively to a result of said step of filtering, wherein said alarm includes a portion of at least one of said first and second signals immediately prior to an incidence of said alarm.

15. A method of monitoring a person, comprising the steps of:

detecting first and second events occurring in said person's environment an said person's state or behavior temporally close to at least one of said first and second events;

generating first and second signals, respectively, responsive to a change in said user's state or behavior temporally close to at least one of said first and second events;

said first and second events being distinct in a way other than by the time of incidence;

filtering said first and second signals through a network classifier;

generating an output signal from said network classifier responsively to said step of filtering.

16. A method as in claim 15, further comprising the step of generating an alarm signal responsively to said step of detecting.

17. A device as in claim 16, wherein said alarm signal is in the form of a symbolic representation of said changed state.

18. A method as in claim 15, wherein said step of detecting a first event includes capturing an image and processing said image, said first signal being responsive to a result of said step of processing.

19. A method of monitoring an unsupervised person living at home, comprising the steps of:

classifying image data to detect a change in one of a mental state and a health status;

classifying audio data to further detect said one of a mental state and a health status;

classifying an alarm state responsive to both said first step of classifying and said second step of classifying; and generating an alarm signal responsive to said third step of classifying, wherein said alarm includes a portion of at least one of said image and audio data immediately prior to an incidence of said alarm signal.

* * * * *